United States Patent [19]

Okawa et al.

[11] Patent Number: 5,196,572
[45] Date of Patent: Mar. 23, 1993

[54] PROCESS FOR PRODUCING XYLYLENE DIISOCYANATE

[75] Inventors: Takashi Okawa; Yoshifumi Sato; Hideo Igarashi; Syunsuke Suzuki, all of Niigata, Japan

[73] Assignee: Mitsubishi Gas Chemical Company, Inc., Osaka, Japan

[21] Appl. No.: 790,038

[22] Filed: Nov. 12, 1991

[30] Foreign Application Priority Data

Dec. 20, 1990 [JP] Japan .................................. 2-411820

[51] Int. Cl.⁵ ........................................... C07C 263/04
[52] U.S. Cl. ................................... 560/345; 521/159; 560/360
[58] Field of Search ........................................ 560/345

[56] References Cited

U.S. PATENT DOCUMENTS

| | | | |
|---|---|---|---|
| 4,330,479 | 5/1982 | Merger et al. | 560/345 |
| 4,530,796 | 7/1985 | Mattner et al. | 560/345 |
| 4,873,365 | 10/1989 | Luh et al. | 560/345 |
| 4,879,410 | 11/1989 | Singh et al. | 560/344 |

FOREIGN PATENT DOCUMENTS

| | | |
|---|---|---|
| 0234353 | 9/1987 | European Pat. Off. . |
| 0396977 | 11/1990 | European Pat. Off. . |
| 0436800 | 7/1991 | European Pat. Off. . |
| 3204973 | 8/1983 | Fed. Rep. of Germany . |
| 54-88201 | 7/1979 | Japan . |
| 57-158747 | 9/1982 | Japan . |
| 1513193 | 6/1978 | United Kingdom . |

*Primary Examiner*—José G. Dees
*Assistant Examiner*—Vera C. Clarke
*Attorney, Agent, or Firm*—Armstrong, Westerman, Hattori, McLeland & Naughton

[57] ABSTRACT

Xylylene diisocyanate is produced in higher space-time yield with higher selectivity by thermal decomposition of xylylene dicarbamate as an urethane compound, i.e. by subjecting the urethane compound to reactive distillation with a thermal decomposition catalyst of at least one of metals selected from antimony and tin or their compounds in the presence of an inert solvent having a higher boiling point than that of the resulting xylylene diisocyanate under reduced pressure of 1 to 500 mmHg and at 150° to 350° C. and then subjecting the resulting reaction products as distillates to partial condensation outside the reactive distillation system, thereby separately recovering the resulting alcohol and xylylene diisocyanate.

5 Claims, No Drawings

PROCESS FOR PRODUCING XYLYLENE DIISOCYANATE

BACKGROUND OF THE INVENTION

This invention relates to a process for producing xylylene diisocyanate by thermal decomposition of xylylene dicarbamate (which will be hereinafter referred to as XDC) as an urethane compound. Xylelene diisocyanate is a diisocyanate having a high reactivity and a good yellowing resistance, which is useful as a raw material for polyurethane and polyurea.

Xylylene diisocyanate is now commercially produced only by reaction of xylylenediamine with phosgene, that is, by phosgenation process, and no other processes have been commercially practised. The phosgenation process has problems in the handling of toxic phosgene, treatment of by-product hydrogen chloride and corrosion of reactor. Thus, development of another commercial process for producing xylylene diisocyanate has been desired as a substitute.

A process for producing xylylene diisocyanate by thermal decomposition of XDC as an urethane compound is available as a process for synthesizing xylylene diisocyanate without using phosgene. Thermal decomposition of XDC as an urethane compound proceeds even in the absence of a catalyst to produce xylylene diisocyanate, but its space-time yield is low owing to low selectivity and reaction rate.

It is also known that an isocyanate and an alcohol can be obtained by thermal decomposition of an urethane compound according to either gas phase process or liquid phase process. The gas phase process belongs to high temperature reaction with much heat of endothermic reaction. This leads to a difficult design of reactors and consequent poor practicality. On the other hand, various liquid phase processes have been proposed. In order to accelerate the thermal decomposition rate and obtain a polymerizable isocyanate with a higher selectivity in a process for producing an isocyanate compound by thermal decomposition of an urethane compound, it is proposed to use a catalyst or to use a carrier for preventing recombination with alcohol.

For example, British Patent No. 2113673A discloses a process for producing an aromatic isocyanate by thermal decomposition of an urethane compound in the presence of a catalyst containing Ti, Sb, Zr or Sn under an atmospheric pressure or superatmospheric pressure (not reduced pressure), but conversion to isocyanate is found to be very poor.

Japanese Patent Application Kokai (Laid-open) No. 54-88201 discloses use of alkaline earth metals such as Be, Mg, Ca, Ba, Sr and Ra or their compounds as a thermal decomposition catalyst.

EPO No. 323514 discloses a process for producing an aliphatic isocyanate by using a simple substance selected from Mn, Mo, W and Zn or their compounds as a thermal decomposition catalyst.

U.S. Pat. No. 4,873,365 discloses a process for producing an alicyclic isophorone diisocyanate by using $SnO_2$ or CuO, or their mixture in the absence of a solvent.

Japanese Patent Application Kokai (Laid-open) No. 57-158747 discloses a process using a catalyst containing at least one of elements selected from copper group, zinc group, aluminum group, carbon group except carbon, and titanium group, and compounds selected from oxides and sulfides of these elements, and also using an inert gas or a low boiling organic solvent as a carrier for preventing recombination of the resulting isocyanate with the resulting alcohol.

As a result of extensive studies on thermal decomposition of XDC as an urethane compound in the above-mentioned conventional processes, the present inventors have found that acceleration of thermal decomposition takes place in some cases, depending on the kind of catalysts used, and furthermore side reactions such as polymerization reaction is increased at the same time, and thus it is difficult to obtain xylylene diisocyanate at a higher decomposition rate with a higher selectivity in the conventional processes, because it seems that xylylene diisocyanate structurally has both aromatic and aliphatic properties and is particularly more polymerizable among a large number of isocyanates (see British Patent No. 1192859 page 2, lines 67–85).

SUMMARY OF THE INVENTION

An object of the present invention is to provide a process for efficiently producing xylylene diisocyanate by thermal decomposition of XDC as an urethane compound.

As a result of extensive studies on a process for producing xylylene diisocyanate by thermal decomposition of XDC as an urethane compound, the present inventors have found that xylylene diisocyanate can be obtained in high space-time yield with a higher selectivity by reduced pressure reactive distillation with a Sb or Sn catalyst in the presence of an inert solvent and by partial condensation of the resulting vapors of alcohol and xylylene diisocyanate outside the reduced pressure reactive distillation system, and have established the present invention.

The present invention provides a process for producing xylylene diisocyanate by thermal decomposition of XDC as an urethane compound, which comprises subjecting the urethane compound to reactive distillation with a catalyst of at least one of metals selected from antimony and tin or their compounds in the presence of an inert solvent having a higher boiling point than that of the resulting xylylene diisocyanate under reduced pressure of 1 to 500 mmHg and at 150° C. to 350° C. and then subjecting the resulting reaction products as distillates to partial condensation outside the reactive distillation system, thereby separately recovering the resulting alcohol and xylylene diisocyanate.

DETAILED DESCRIPTION OF THE INVENTION

The present invention will be described in detail below:

XDC for use in the present invention is in an adduct form of xylylene diisocyanate and alcohol.

Alkyl group of the alcohol preferably contains not more than 8 carbon atoms from the view point of easy separation from xylylene diisocyanate, and includes, for example, methyl, ethyl, propyl, isopropyl, butyl, isobutyl, amyl, isoamyl, hexyl, heptyl and octyl, and particulary preferably is methyl. That is, dimethyl xylylene dicarbamate is preferably used as a methyl ester. The XDC includes three isomers, that is, oisomer, m-isomer and p-isomer, which can be used alone or in their mixture. The XDC can be prepared (1) by reaction of xylylenediamine with carbon monoxide and oxygen in the presence of alcohol, (2) by reaction of xylylenediamine with carbamic acid ester or reaction of xylylenediamine with urea and alcohol, or (3) by reaction of xylylenediamine or phenylenebis(methylene)bisformamide and dimethyl carbonate.

Catalyst for use in the present invention is at least one of metals selected from antimony and tin, or their compounds. The antimony compound includes, for example, antimony trioxide, antimony tetraoxide, antimony pentaoxide, antimony trichloride, antimony pentachloride, antimony oxychloride, antimony tribromide, antimony triiodide, antimony sulfate, triphenylantimony, pentaphenylantimony and triphenylantimony dichloride. The tin compound includes, for example, stannous oxide, stannic oxide, stannous chloride, stannic chloride, stannous bromide, stannic bromide, stannous iodide, stannic iodide, stannous acetate, stannous oxalate, stannous stearate, stannous oleate, stannous sulfate, and stannous phosphate. The catalyst is used in an amount of 0.0001 to 10% by weight, preferably 0.001 to 1% by weight, on the basis of the solvent.

Solvent for use in the present invention must be inert at least to the urethane compound and the resulting xylylene diisocyanate compound and must have a higher boiling point than that of the resulting xylylene diisocyanate. In order to selectively withdraw the alcohol and xylylene diisocyanate generated by thermal decomposition of the urethane compound to the outside of the reactive distillation system, it is preferable to use a solvent having a large difference in the boiling point, for example, a difference by at least 40° C. Without using any inert solvent, side reaction such as polymerization of the resulting xylylene diisocyanate considerably proceeds, so that xylylene diisocyanate cannot be substantially obtained. Without withdrawing the xylylene diisocyanate formed by the thermal decomposition of the urethane compound rapidly and partially condensing it outside the reactive distillation system, it is hard to obtain xylylene diisocyanate in high yield due to higher side reaction rate such as the polymerization rate even in the presence of the solvent. The solvent includes, for example, aromatic esters such as dioctyl phthalate, didecyl phthalate, didodecyl phthalate, and diphenyl phthalate, and aromatic hydrocarbons such as aromatic petroleum fractions frequently used as a heating medium, for example, dibenzyltoluene, pyrene, triphenylmethane, phenylnaphthalene and benzylnaphthalene. The solvent is used in an amount of 0.1 to 100 parts by weight, preferably 0.5 to 50 parts by weight, to the urethane compound as a raw material.

The present invention is carried out by reactive distillation which comprises thermally decomposing an urethane compound in the presence of a catalyst and a solvent and partially condensing the resulting xylylene diisocyanate and alcohol outside the reactive distillation system. Thermal decomposition temperature of an urethane compound is in a range of 150° to 350° C., preferably 200° to 300° C. Operating pressure is a pressure under which the xylylene diisocyanate and alcohol formed at the thermal decomposition temperature can be vaporized, that is, 1 to 500 mmHg, preferably 5 to 50 mmHg (hereinafter, as a pressure unit, absolute pressure is used). The present invention can be carried out batchwise, but continuous operation of feeding a molten urethane compound to a solvent containing a catalyst under a reduced pressure is preferable. The resulting vapors of xylylene diisocyanate and alcohol formed by the thermal decomposition of an urethane compound are separated into xylylene diisocyanate and alcohol, respectively and recovered by a difference in the condensation temperatures of the respective distillates.

DESCRIPTION OF THE PREFERRED EMBODIMENTS

Example 1

A 200-ml, three-necked, round bottom flask with a capillary tube, a thermometer and a fractionating head provided with a reflux condenser was used as a reactor. A receptacle was provided at the fractionating head, and warm water at 60° C. was passed through the reflux cooler. The top of the reflux cooler and the receptacle were connected to a vacuum line through a cold trap cooled with methanol-dry ice.

15 g of dimethyl 1,3-xylylene dicarbamate (which will be hereinafter referred to as MXDC), 0.075 g of antimony trioxide, and 150 g of Marlotherm S (main component: dibenzyltoluene, trademark of a product made by Hüls) as a solvent were charged into the flask. The flask was placed in a mantle heater, flushed with a nitrogen gas and heated to a flask inside temperature of 230° C. under reduced pressure of 20 mmHg. The vapors generated at that temperature were trapped in the cold trap. Three hours after the heating, the liquids remaining in the reactor, receptacle and cold trap were analyzed by liquid chromatography and gas chromatogarphy. It was found that yield of meta-xylylene diisocyanate (which will be hereinafter referred to as MXDI) was 82.6% and yield including the intermediate of monoisocyanate was 94.6%, whereas unreacted MXDC was not found.

Example 2

Catalyst activity test was carried out in the same manner as in Example 1, using 0.075 g of stannic oxide in place of antimony trioxide. It was found that MXDI yield was 83.5% at MXDC conversion of 99.5%, and yield including the intermediate of monoisocyanate was 96.7%.

Comparative Example 1

Reaction was carried out in the same manner as in Example 1 without using any antimony trioxide. It was found that MXDI yield was 32.8% at MXDC conversion of 66.3%, and yield including the intermediate of monoisocyanate was 61.9%.

Comparative Example 2

Into a 200-ml, three-necked, round bottom flask with a thermometer and an air-cooled tube were charged 15 g of MXDC, 0.075 g of antimony trioxide and 50 g of Marlotherm S. The flask was placed in a mantle heater and subjected to thermal decomposition reaction under the atmospheric pressure at 230° C. for 3 hours, while passing a nitrogen gas through the flask at a rate of 10 l/hr. After cooling, the reaction product solution was analyzed and it was found that MXDI yield was 15.7% at MXDC conversion of 90.2% and yield including the intermediate of monoisocyanate was 24.4%. Polymers were found in the flask.

Comparative Example 3

15 g of MXDC and 0.075 g of antimony trioxide were charged into the same flask as used in Example 1 and subjected to thermal decomposition reaction under a pressure of 20 mmHg at 230° C. in the absence of a solvent. It was found that polymerization reaction took place in the flask and no MXDI was obtained at all.

Comparative Examples 4 to 29

Catalyst activity tests were carried out in the same manner as in Example 1, using 0.075 g of various metals and metal compounds as catalysts as shown in Table 1. Results are shown in Table, where those of Examples 1 and 2 are also given. Example 3

Catalyst activity test was carried out in the same manner as in Example 1, using 0.045 g of triphenylantimony in place of the antimony trioxide. The reaction proceeded in a homogeneous system and it was found that MXDI yield was 84.0% at MXDC conversion of 98.0%, and yield including the intermediate of monoisocyanate was 94.1%.

Example 4

Catalyst activity test was carried out in the same manner as in Example 2, using 0.006 g of stannous acetate in place of the stannic oxide. Reaction proceeded in a homogeneous system and it was found that MXDI yield was 89.9% at MXDC conversion of 95.1% and yield including the intermediate monoisocyanate was 94.9%.

Example 5

Into a 500-ml, four-necked flask with a capillary tube, a thermometer and a packed column provided with a fractionating head (packed with 170 cc of Dixon packings, 25 mm in diameter x 350 mm long) were charged 460 g of Marlotherm S and 0.16 g of triphenylantimony. Then, the flask was placed in a mantle heater. The fractionating head was provided with a receptacle and a reflux condenser, through which warm water at 60° C. was passed. The top of the reflux condenser and the receptacle were connected to a vacuum line through a cold trap cooled with methanol-dry ice. Then, the flask was kept at 20 mmHg and 250° C. and MXDC in a molten state was dripwise added to the flask at a feed rate of 25 g/hr through a dropping funnel. The formed MXDI and methanol were trapped in the receptacle and the cold trap. The raw material MXDC was continuously charged into the flask for 8 hours, and operation was discontinued after complete removal of MXDI from the reactive distillation system by the reactive distillation. The distillates and the liquid remaining in the flask were analyzed, and it was found that MXDI yield was 95.6% at MXDC conversion of 97.5% and yield containing the intermediate of monoisocyanate was 96.6%.

Example 6

Catalyst reactivity test was carried out in the same manner as in Example 5, using 0.02 g of stannous acetate in place of the triphenylantimony. It was found that MXDI yield was 95.0% at MXDC conversion of 98.1% and yield including the intermediate of monoisocyanate was 96.4%.

Example 7

Catalyst reactivity test was carried out in the same manner as in Example 5, using dimethyl-1,4xylylene dicarbamate (which will be hereinafter referred to as PXDC) in place of the MXDC. It was found that para-xylyene diisocyanate yield was 93.7% at PXDC conversion of 97.0% and yield including the intermediate of monoisocyanate was 95.2%.

Comparative Example 30

Thermal decomposition reaction was carried out in the same flask as used in Example 1 under reduced pressure of 20 mmHg and at 230° C. by charging 15 g of MXDC, 0.075 g of antimony trioxide and 150 g of silicone oil (KF965, trademark of a product made by Shinetsu Kagaku Kogyo K.K., Japan) as a non-inert solvent having a higher boiling point than that of MXDI. It was found that there appeared foaming phenomena and polymerization in the flask, and no meta-xylylene diisocyanate was obtained.

TABLE

| Catalyst | MXDC conversion (%) | MXDI yeild (%) | MXDI + MXMI yield (%) |
|---|---|---|---|
| Example | | | |
| 1  $Sb_2O_3$ | 100 | 82.6 | 94.6 |
| 2  $SnO_2$ | 99.5 | 83.5 | 96.7 |
| Comp. Ex. | | | |
| 1  — | 66.3 | 32.8 | 61.9 |
| 4  MgO | Polymerixed | | |
| 5  $Y_2O_3$ | 38.6 | 9.5 | 35.5 |
| 6  $TiO_2$ | 74.4 | 14.4 | 44.1 |
| 7  $ZrO_2$ | 68.0 | 15.7 | 39.9 |
| 8  $VO(AA)_2$ | polymerized | | |
| 9  $V_2O_5$ | 88.9 | 44.2 | 63.4 |
| 10 $WO_3$ | 58.9 | 12.3 | 46.4 |
| 11 $MoO_2(AA)$ | 61.4 | 16.3 | 42.1 |
| 12 $MoO_3$ | 65.2 | 23.7 | 55.9 |
| 13 $CrO_3$ | 53.9 | 10.3 | 36.1 |
| 14 $Mn(CH_3COO)_2$ | polymerized | | |
| 15 $Mn(AA)_2$ | polymerized | | |
| 16 $MnO_2$ | 92.0 | 26.7 | 36.6 |
| 17 $CuCl_2$ | 94.5 | 9.2 | 25.7 |
| 18 CuO | 78.6 | 29.1 | 55.0 |
| 19 $ZnCl_2$ | polymerized | | |
| 20 $Al_2O_3$ | 49.3 | 11.8 | 46.2 |
| 21 $Ga_2O_3$ | 49.6 | 11.6 | 48.9 |
| 22 $In_2O_3$ | 68.3 | 36.4 | 62.9 |
| 23 Carbon | 61.7 | 22.4 | 59.4 |
| 24 $SiO_2$ | 59.6 | 17.5 | 53.6 |
| 25 $GeO_2$ | 50.6 | 7.0 | 41.5 |
| 26 PbO | polymerized | | |
| 27 $Fe(AA)_3$ | polymerized | | |
| 28 $Fe_2O_3$ | 79.2 | 39.4 | 23.2 |
| 29 NiO | 62.1 | 11.7 | 44.5 |

(Note)
Abbreviations in Table are as follows:
MXDC: Dimethyl-1,3-xylylene dicarbamate
MXDI: Meta-xylylene diisocyanate
MXMI: 3-isocyanatomethyl 1-methoxycarbonylamino-methyl phenylene
AA: $CH_3COCHCOCH_3$ According to the present invention, xylylene diisocyanate can be produced in higher space-time yield with good selectivity by thermal decomposition of XDC that can be readily prepared from xylylenediamine. The present invention has no problems in the handling of toxic phosgene, treatment of by-produced hydrogen chloride and corrosion of reactor, as compared with the current phosgenation process, and thus can provide a commercially distinguished process.

Though British Patent No. 2113673A discloses a thermal decomposition process under the atmospheric pressure or a superatmospheric pressure (not reduced pressure) in the presence of a catalyst containing Ti, Sb, Zr or Sn, the conversion to the isocyanate is very low, as mentioned before.

In the present invention, on the other hand, xylylene diisocyanate can be obtained with a very high conversion, as shown in the foregoing Examples, when reactive distillation is carried out under reduced pressure of 1 to 500 mmHg and 150° C. to 350° C. by using a catalyst of at least one of metals selected from antimony and tin among various metals or their compounds in the presence of an inert solvent having a higher boiling point than that of the resulting xylylene diisocyanate. In case of other metal catalysts than antimony and tin, for example, Ti or Zr disclosed in British Patent No. 2113673A, isocyanate cannot be obtained in higher yield, as shown in the foregoing Comparative Examples, even if reactive distillation is carried out under reduced pressure and at 150° to 350° C. in the presence of the present inert solvent. When a catalyst of antimony or tin is used without using the present inert solvent, polymerization reaction takes place and no xylylene diisocyanate is obtained at all, as shown in Comparative Example 3. When other solvent than the present inert solvent is used, polymerization reaction takes place likewise and no xylylene diisocyanate is obtained at all, either, as shown in Comparative Example 30.

Thus, in the production of isocyanates, particularly xylylene diisocyanate, xylylene diisocyanate can be obtained with higher conversion and selectivity by combination of the present catalyst based on at least one of antimony and tin, the present inert solvent, the present reactive distillation conditions such as a reduced pressure and a temperature of 150° C. to 50° C., and partial condensation of products outside the reactive distillation system.

What is claimed is:

1. A process for producing xylylene diisocyanate by the thermal decomposition of xylylene dicarbamate, which comprises subjecting the xylylene dicarbamate to reactive distillation in a reaction system at a temperature of 200-300° C. and at a pressure of 1-500 mm Hg with a thermal decomposition catalyst comprising at least one of antimony, tin or a compound thereof, in the presence of an inert solvent having a boiling point at least 40° C. higher than that of the xylylene diisocyanate being produced, withdrawing vapors of the xylylene diisocyanate and of the alcohol formed by the thermal decomposition of the xylylene dicarbamate from the reaction system, and separately condensing the vapors of the xylylene diisocyanate and of the alcohol.

2. A process for producing xylylene diisocyanate by the thermal decomposition of xylylene dicarbamate to form the xylylene diisocyanate and an alcohol, which comprises subjecting the xylylene dicarbamate to reactive distillation in a reaction system at a temperature of 200-300° C. and at a pressure of 1-500 mm Hg with a thermal decomposition catalyst comprising antimony or a compound thereof, in the presence of an inert solvent having a boiling point at least 40° C. higher than that of the xylylene diisocyanate being produced, withdrawing vapors of the xylylene diisocyanate and of the alcohol formed by the thermal decomposition of the xylylene dicarbamate from the reaction system, and separately condensing the vapors of the xylylene diisocyanate and of the alcohol.

3. A process according to claim 1 or 2, wherein the inert solvent is used in an amount of 0.1 to 100 parts by weight to the xylylene dicarbamate.

4. A process according to claim 1 or 2, wherein the thermal decomposition catalyst is used in an amount of 0.0001 to 10% by weight on the basis of the inert solvent.

5. A process according to claim 1 or 2, wherein the inert solvent is an aromatic ester or an aromatic hydrocarbon.

* * * * *